United States Patent … (12) United States Patent
Von Schuckmann

(10) Patent No.: US 7,448,342 B2
(45) Date of Patent: Nov. 11, 2008

(54) STEP-ACTION INDEXING MECHANISM

(76) Inventor: Alfred Von Schuckmann, Winnekendonker Str. 52, D-47627 Kevelaer (DE)

(*) Notice: Subject to any disclaimer, the term of this patent is extended or adjusted under 35 U.S.C. 154(b) by 0 days.

(21) Appl. No.: 11/747,013

(22) Filed: May 10, 2007

(65) Prior Publication Data

US 2007/0235027 A1 Oct. 11, 2007

Related U.S. Application Data

(63) Continuation of application No. PCT/EP2005/055823, filed on Nov. 8, 2005.

(30) Foreign Application Priority Data

| Nov. 10, 2004 | (DE) | ......................... 10 2004 054 179 |
| Jul. 18, 2005 | (DE) | ......................... 10 2005 033 398 |

(51) Int. Cl.
*A61M 15/00* (2006.01)
*B65D 83/14* (2006.01)

(52) U.S. Cl. ..................... 116/307; 128/205.23; 222/36

(58) Field of Classification Search .............. 116/298, 116/299, 307, 309, 312, 316, 317; 128/200.14, 128/200.23, 205.23; 222/36, 38; 235/91 R
See application file for complete search history.

(56) References Cited

U.S. PATENT DOCUMENTS

| 5,228,586 | A |   | 7/1993 | Fuchs ........................... 222/38 |
| 5,971,140 | A |   | 10/1999 | Frutin ......................... 206/222 |
| 5,988,496 | A | * | 11/1999 | Bruna ....................... 235/91 R |
| 6,164,494 | A | * | 12/2000 | Marelli .......................... 222/38 |
| 6,283,365 | B1 | * | 9/2001 | Bason .......................... 235/116 |
| 6,431,168 | B1 |   | 8/2002 | Rand et al. ............. 128/200.23 |
| 7,195,134 | B2 | * | 3/2007 | Ouyang et al. ................. 222/36 |
| 2003/0178020 | A1 |   | 9/2003 | Scarrott ................. 128/200.23 |
| 2004/0149772 | A1 | * | 8/2004 | Ouyang ........................ 222/36 |
| 2004/0149773 | A1 | * | 8/2004 | Ouyang et al. ................. 222/36 |
| 2004/0211420 | A1 |   | 10/2004 | Minshull et al. ........ 128/203.15 |
| 2005/0017020 | A1 | * | 1/2005 | Eckert .......................... 222/30 |
| 2005/0209558 | A1 | * | 9/2005 | Marx ....................... 604/97.03 |
| 2007/0240708 | A1 | * | 10/2007 | Schuckmann .......... 128/200.14 |

FOREIGN PATENT DOCUMENTS

| EP |   | 0 480 488 A1 |   | 4/1992 |
| EP |   | 1 065 477 A2 |   | 1/2001 |
| FR |   | 2858867 A1 | * | 2/2005 |
| GB |   | 1317315 |   | 5/1973 |
| WO |   | WO 01/28887 A1 |   | 4/2001 |

OTHER PUBLICATIONS

International Search Report, Mar. 21, 2006, 2 pages.

* cited by examiner

*Primary Examiner*—R. A. Smith
(74) *Attorney, Agent, or Firm*—St. Onge Steward Johnston & Reens LLC

(57) ABSTRACT

The invention relates to a step-by-step mechanism, particularly for hand-held devices for the portioned delivery of medicaments to be inhaled, comprising a graduated collar, which can be moved during an actuation stroke and which encircles the center axis of the housing. In order to provide a step-by-step mechanism of the aforementioned type with a more reliable operation while, in a spatially advantageous manner, having a simplified design, the invention provides that the switching finger(s) are permitted to slope upward from a hub located in the center.

8 Claims, 6 Drawing Sheets

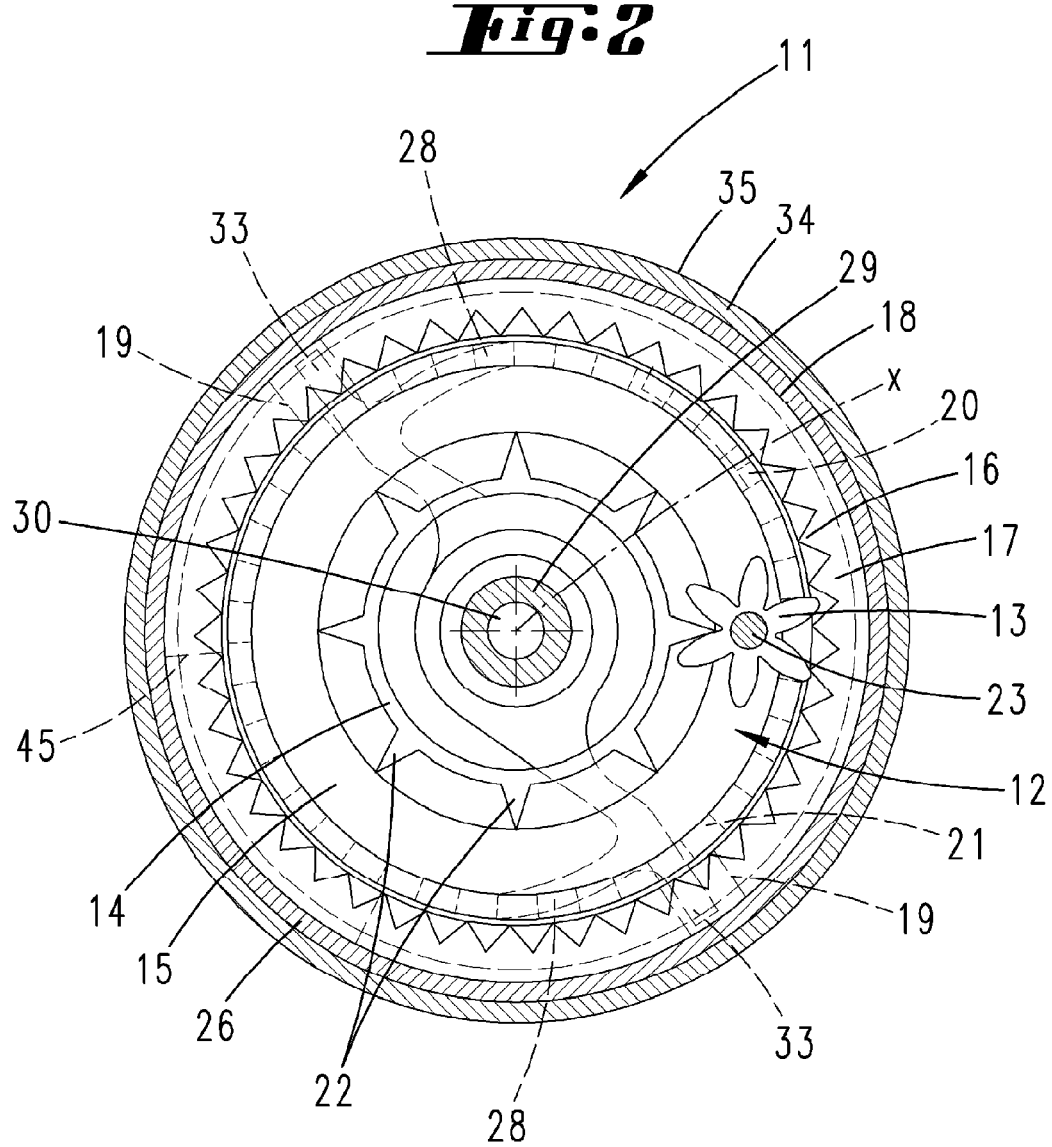

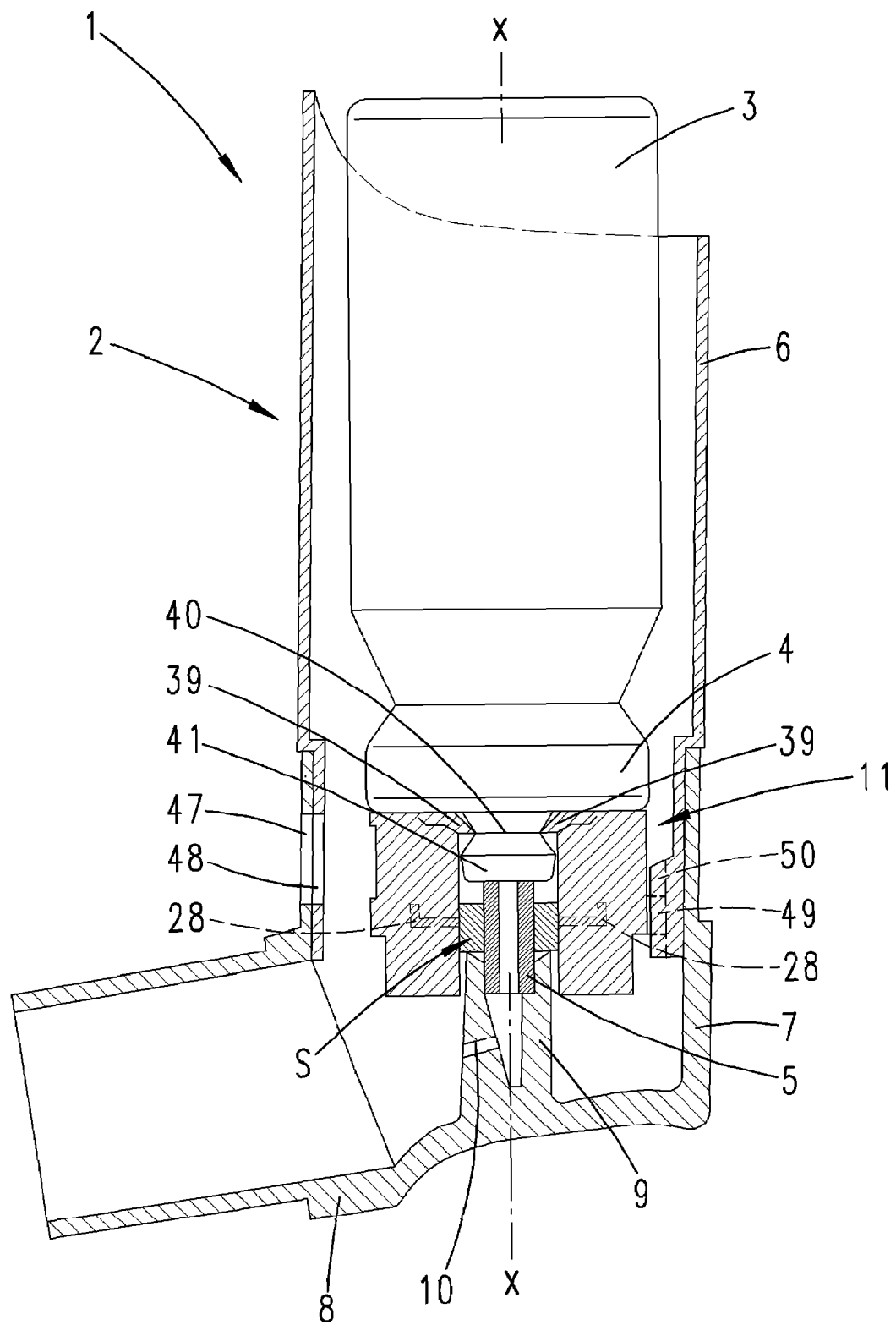

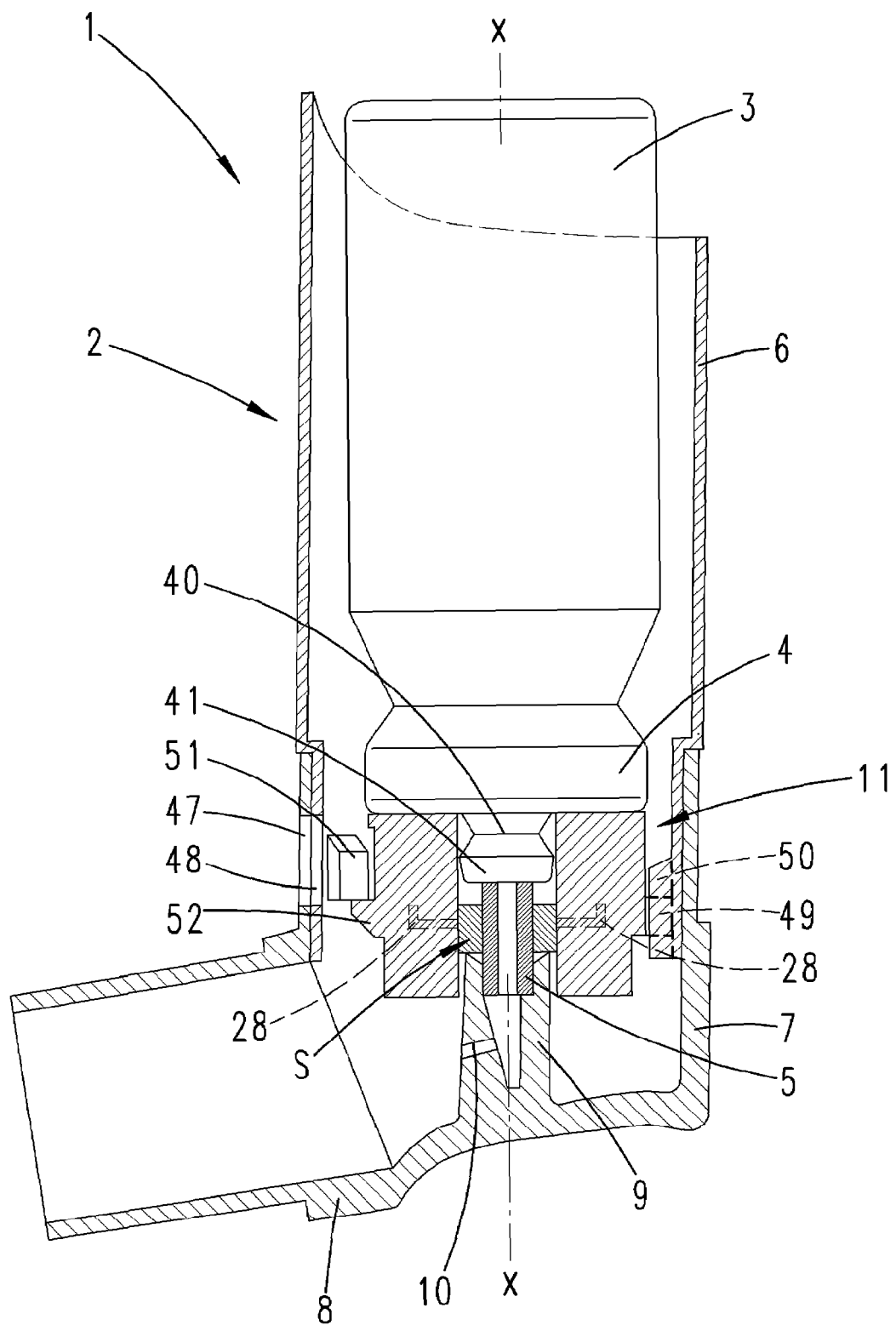

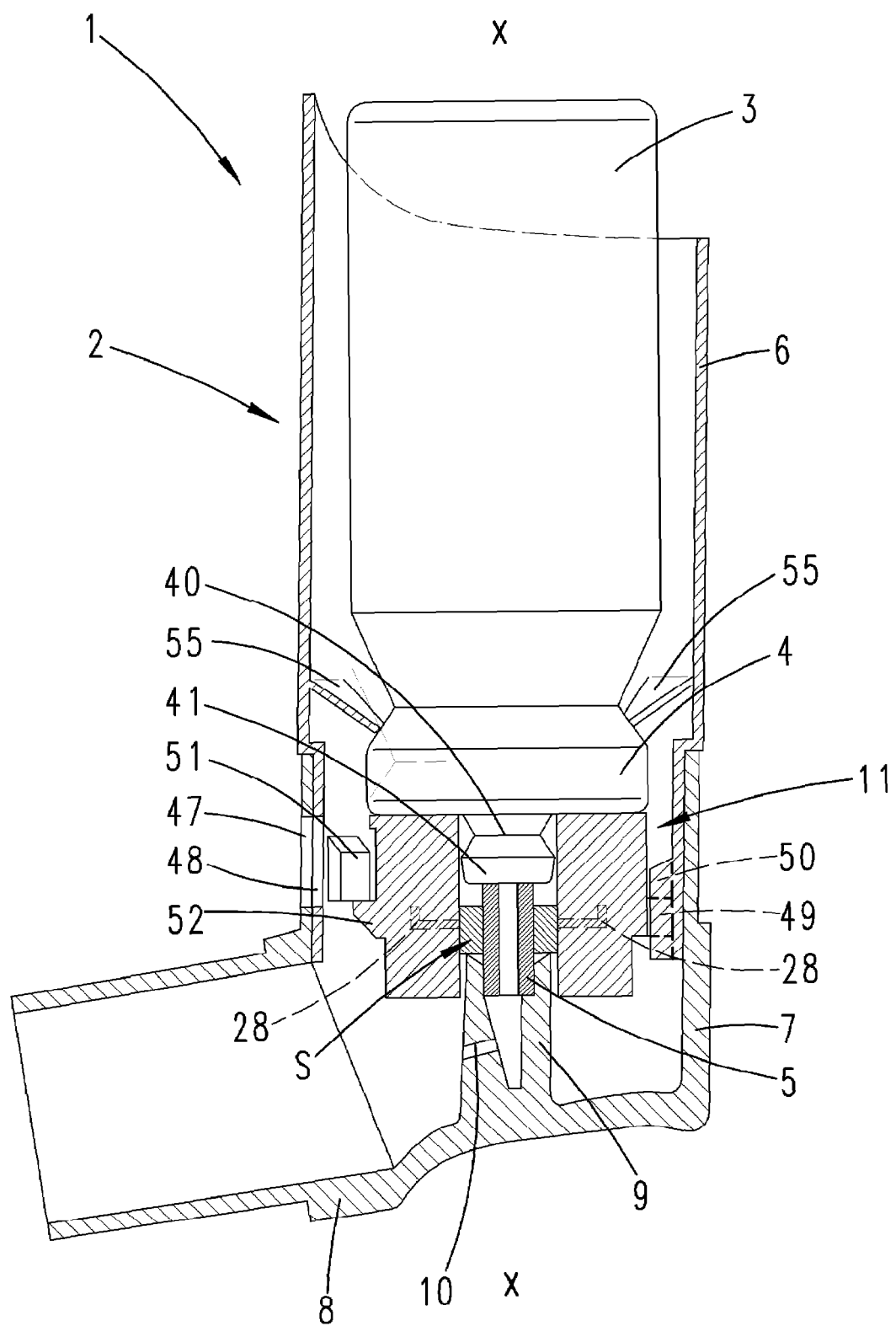

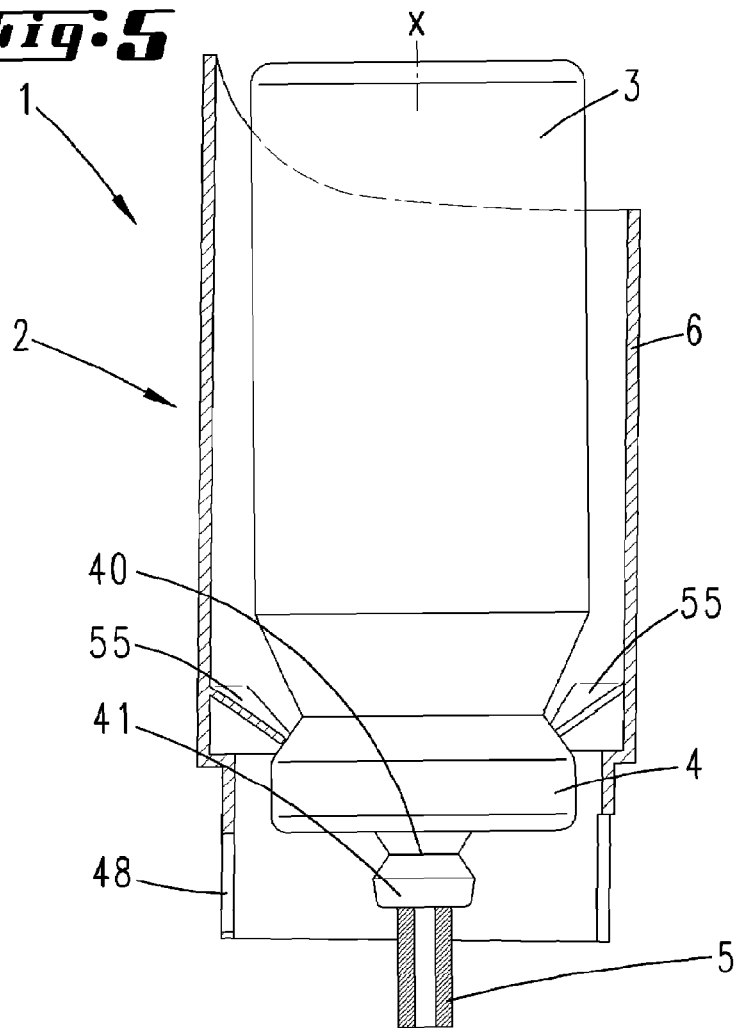
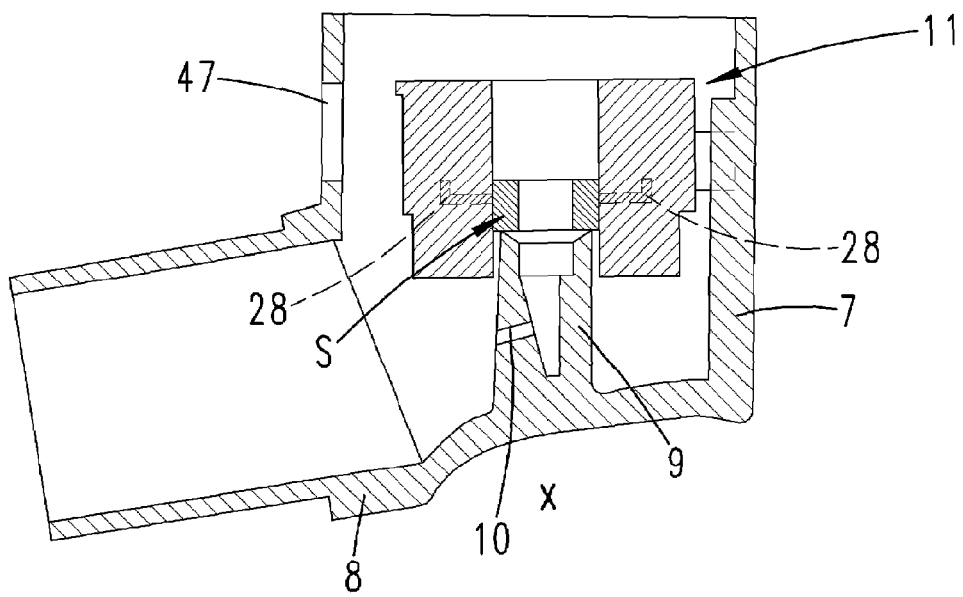

STEP-ACTION INDEXING MECHANISM

CROSS-REFERENCE TO RELATED APPLICATIONS

The present application is a continuation of pending International patent application PCT/EP2005/055823 filed on Nov. 8, 2005 which designates the United States and claims priority from German patent applications Nos. 10 2004 054 179.5 filed on Nov. 10, 2004 and 10 2005 033 398.2 filed on Jul. 18, 2005. All prior applications are herein incorporated by reference.

FIELD OF THE INVENTION

The invention relates to a step-action indexing mechanism according to the preamble of the main claim.

BACKGROUND OF THE INVENTION

Such step-action indexing mechanisms e.g. configured in accordance with GB 1317315, are used in particular in medical aerosol therapy for the treatment of respiratory conditions. A pressurized cartridge located in the unit contains the medicament which is to be inhaled. In order for the latter to be expelled, it is necessary for the cartridge to be displaced axially in the unit. The unit, which usually more or less fully encloses the cartridge, also conventionally has a mouthpiece and/or an adapter for inhaling through the nose. It is necessary to provide the user with a counter for indicating the quantity of medicament which has been used or is still present in the cartridge. Since a defined quantity of medicament is discharged upon each cartridge actuation, it is known for the medicament is discharged upon each cartridge actuation, it is known for the counter to be coupled to the axial displacement of the cartridge in the inhaler housing for the purpose of discharging medicaments. The generically determined solution, which is known for this purpose, is too large to be accommodated in normal units. Moreover, it is difficult to assemble, in particular in respect of the step-action indexing fingers, which are mounted on transverse pins in relation to the step-action indexing-mechanism housing and are to be loaded by separate springs. The counting accuracy which can be achieved is insufficient for use with medicaments. Upon insertion or removal, e.g. for cleaning purposes, incorrect counting can easily take place such that the step-action counter counts a step which did not actually constitute a dispensing step in the inhaler.

An inhaler appliance is known from EP 480488 with an upper cap which is displaceable in the direction of a cartridge, which cap surrounds an annular part from which there extend obliquely, oppositely-directed resilient step-action indexing fingers, the ends of which engage in a toothed rim, when the cap is pushed in the direction of the cartridge, so that the linear displacement of the cap is converted into a rotational movement of a scale ring. The rotation of the scale ring is visible through a window provided on the cap. The solution is costly and is in particular very disadvantageous in respect of cleanability.

It is also the case elsewhere that there is a need for straightforwardly constructed counters which operate independently.

In respect of the above described prior art, a technical problem addressed by the invention is considered as that of configuring a step-action indexing mechanism of the type in question in a spatially advantageous manner, along with simplified construction, such that it is more reliable to handle.

SUMMARY OF THE INVENTION

This problem is solved first and foremost by the subject matter of Claim 1, this being based on an annular housing with indexing members which encircle axes positioned in the longitudinal direction of the housing. The step-action indexing mechanism fits in front of the lower end of corresponding (standard) cartridges of a medicament inhaler and can enclose the outlet tubule thereof. The construction selected requires only a very small amount of space and is also formed advantageously as far as cleaning possibilities and moreover as far as handling during cleaning are concerned. For all practical purposes, counting is not possible outside the inhaler or the like. Functioning is ensured merely by purely mechanically interacting components which, in addition, may further preferably consist of a single plastics material. This helps to simplify production, in particular as far as assembly is concerned. The indexing mechanism is completely independent, that is to say it need not be carried along by other parts, such as a cartridge. These indexing fingers also execute the return movement following actuation.

The subject matters of the rest of the claims are explained in relation to the subject matter of the main claim, and present advantageous developments.

It is thus further provided that the step-action indexing mechanism has a concentrically encircling ring with a scale on its outside, the ring being rotated, via a planet-gear mechanism, by a likewise concentrically encircling toothed rim which is driven by the actuating stroke. The rotary movement of the scale ring is derived from a relative displacement of the step-action indexing mechanism. The indexing finger of the latter operates on a path around the center. All that is required is to provide a supporting portion for the indexing-finger hub. In the case of the step-action indexing mechanism possibly being removed from a unit, accidental actuation of the step-action indexing mechanism is not possible on account of the supporting portion for the indexing finger no longer being present. The step-action indexing mechanisms can be packed, and sold, as bulk goods. Furthermore, it is provided that the planet gear is mounted in a bore of the scale ring, and the associated sun gear is seated on a disk which is toothed on the underside. This disk is in engagement with the indexing finger. Furthermore, a latching finger engages in the toothing formation in order to secure the rotary position of the disk which has been reached in each case. The sun gear and toothed disk are preferably formed as a single part, with coaxial alignment. The planet-gear mechanism preferably passes on the angle of rotation to the scale ring in stepped-down form. 200 or 300 stroke actions can correspondingly be shown on the scale ring. It is further preferred if the graduated scale of the scale ring, the scale being disposed on the outer lateral surface of the scale ring and extending in front of a viewing window of the housing, corresponds in each case to a number of individual rotary steps of the planet gear. In this respect, it proves to be advantageous, furthermore, if, as far as the step-down transmission is concerned, an individual rotary step of the planet gear takes place following a number of individual rotary steps of the sun gear. The planet gear, furthermore, is in engagement, in the radially outward direction, with a toothed rim. This arrests the respective rotary position of the scale ring. A slot which extends, directed obliquely upward, from the lower peripheral edge, for the insertion of the step-action indexing finger, is provided in order to predetermine thereby the indexing direction of the finger for rotating the disk on the sun gear further in a stepwise manner. The step-action indexing finger or fingers is or are a constituent part of a step-action indexing-finger star, which has a central hub on which step-action indexing fingers are integrally formed, these fingers being located diametrically opposite one another at a radial spacing from the hub. This step-action indexing-finger star is preferably formed in one piece, preferably from a plastics material. The step-action indexing fingers are directed to extend obliquely upward from the hub, the step-action indexing fingers, furthermore, moving in the direction of a plane perpendicular to the longitudinal axis during the actuating stroke. Accordingly, the step-action indexing fingers are subjected to stressing during the dispensing movement, i.e. during the displacement, for example, of a cartridge along its longitudinal center axis. The step-action indexing-mechanism housing as a whole moves in this case. When used in normal inhalers, the hub of the step-action indexing-finger star can be seated on the end surface of the supporting portion on the hand-held-unit housing. This supporting portion then has a dual function: on the one hand, it functions as a triggering element in conjunction with the valve tube of the cartridge and, on the other hand, the supporting portion has the function of an abutment for the step-action indexing-finger star. This means that there is no possibility at all of actuating the step-action indexing mechanism outside a unit. The step-action indexing-mechanism housing with the rest of the indexing members is displaced relative to the step-action indexing-finger star, this involving movement of the step-action indexing fingers into the plane oriented perpendicularly to the longitudinal axis, which gives rise to the above described prestressing of the step-action indexing fingers and the advancement of the counter. Following release of the actuating pressure, the fingers return into their starting position again. This is achieved by the prestressed step-action indexing fingers which automatically resume their original, obliquely upwardly directed position and, in the process, force the indexing members and the step-action indexing-mechanism housing into their original positions. Correspondingly, in respect of the return displacement into a starting position, the step-action indexing mechanism is decoupled from the cartridge. It has a restoring spring formed by the step-action indexing fingers. It is preferable for the entire step-action indexing mechanism, together with the scale ring, to be enclosed in a round housing, which once again proves to be advantageous in respect of the desired cleaning of the housing. There are no gear-mechanism parts exposed which could be damaged during cleaning, for example by brushing. Rather, a compact, substantially closed construction is selected. In this respect, it is further proposed that the step-action index-mechanism housing, which is configured as a flat plate, has a central hole for the through-passage of a component. It is also possible, in addition, for the step-action index-mechanism housing to be secured—as is known—on the cartridge in the center, beneath the end wall at the opening end and so as to overlap the cartridge valve tube, by resilient latching.

BRIEF DESCRIPTION OF THE DRAWINGS

The invention will be explained in more detail hereinbelow with reference to the accompanying drawing, which merely illustrates various exemplary embodiments and in which:

FIG. 2 shows a cross-section through the step-action indexing mechanism;

FIG. 3 shows a longitudinal section through a hand-held inhaler unit with a schematically illustrated step-action indexing mechanism latched on the cartridge thereof;

FIG. 4 shows a sectional illustration corresponding to FIG. 3, but relating to a different solution, in which the schematically illustrated step-action indexing mechanism is latched on a housing;

FIG. 4a shows a modified embodiment in a sectional illustration according to FIG. 4, in the case of which the step-action indexing mechanism in an inhaler is blocked against being pulled out; and FIG. 5 shows a longitudinal section through an inhaler with step-action indexing mechanism inserted, following separation of an upper inhaler housing part from its mouthpiece.

DETAILED DESCRIPTION OF THE INVENTION

Figure 1:
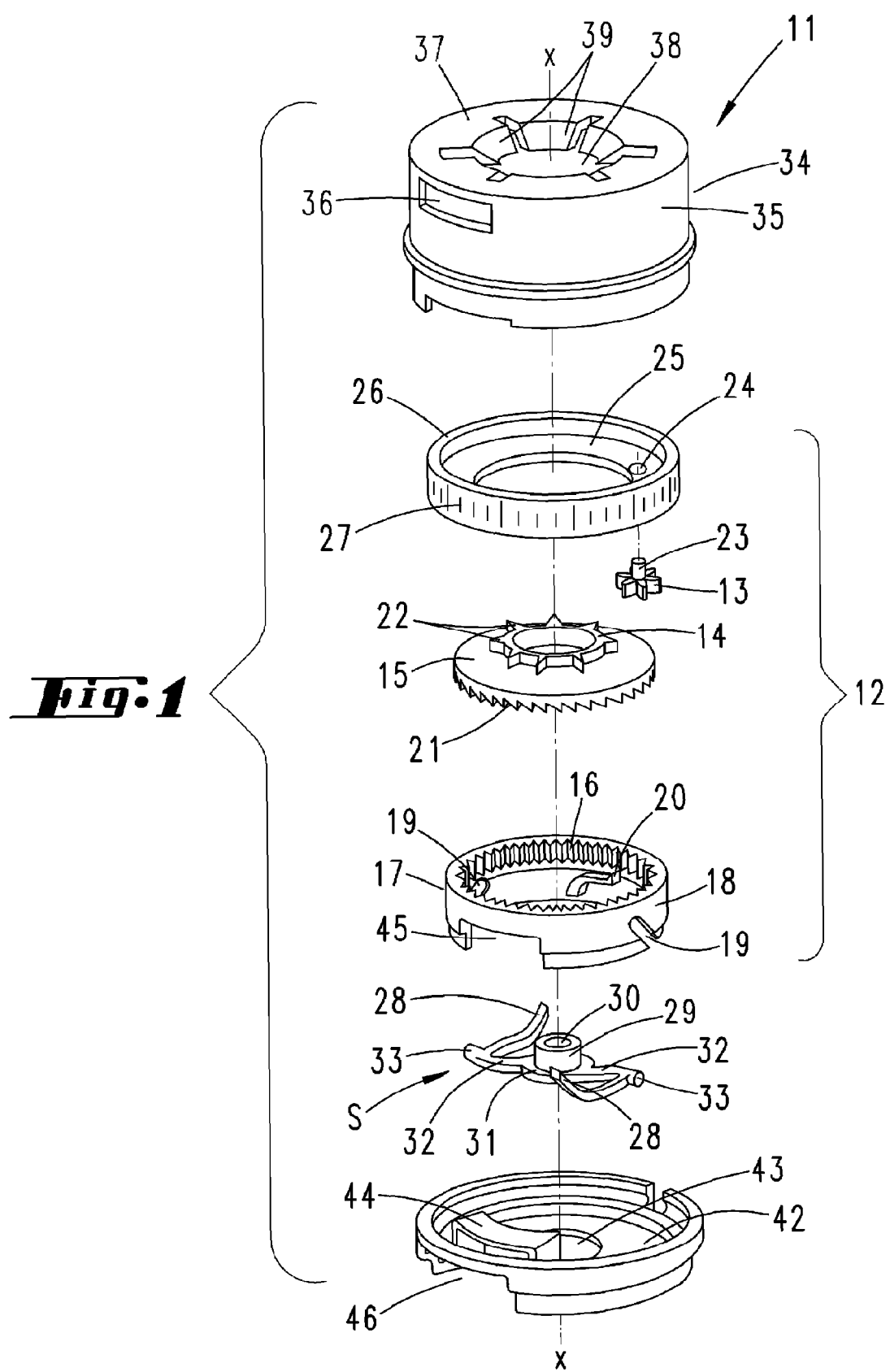
FIG. 1 shows, in exploded perspective illustration, the step-action indexing mechanism for the step-action indexing mechanism according to the invention.

The hand-held unit 1 which is shown in a schematic sectional illustration in FIG. 3 serves for apportioned delivery of sprayable substances, in particular inhaler medicaments.

For this purpose, the hand-held unit 1, in the first instance, has a hand-held-unit housing 2 into which a cartridge 3 containing the sprayable substance can be inserted. This cartridge 3 is axially displaceable in the housing 2. In conventional manner, the cartridge head 4 has a central valve tube 5, which extends coaxially in relation to the cartridge 3. A delivery of medicament is achieved via this valve tube by an axial relative movement between the cartridge 3 and housing 2. The inhaler housing 2 is in two parts and comprises two annular parts 6 and 7 which are disposed one above the other and of which the upper annular part 6 is formed as a passageway and the lower annular part 7 has a mouthpiece 8 oriented approximately transversely to the extent of the passageway. This mouthpiece can be closed by a covering cap (not illustrated). The valve tube 5 of the cartridge 3 is supported in an associated tubular supporting portion 9 within the lower annular part 7, it being possible for the cartridge 3 to move axially within the passage-form annular part 6, which surrounds the cartridge 3. The supporting portion 9, which accommodates the valve tube 5 of the cartridge 3 with clamping action and is formed within the lower annular housing part 7, is provided with a flow channel 10 which has a smaller diameter than a portion accommodating the valve-tube end and is connected to the valve tube 5 in terms of flow, that end of the flow channel 10 which is directed away from the valve tube 5 being oriented in the direction of the mouthpiece 8.

A step-action indexing mechanism 11 is disposed centrally beneath the opening-side end wall of the cartridge 3, so as to overlap the cartridge valve tube 5. This indexing mechanism serves for registering and/or counting/indicating the dispensing actuations which have been executed, in dependence on the opening strokes of the cartridge 3 which have been executed.

The step-action indexing mechanism 11 is shown in FIG. 1 in an exploded perspective illustration. The central constituent part of the step-action indexing mechanism 11 is a planet-gear mechanism 12 consisting of a planet gear 13, a sun gear 14, which is seated on a disk 15 which is toothed on the underside, and a toothed rim 16, which interacts with the planet gear 13 with arresting action. This toothed rim is formed on the inner wall of a ring 17 which is in the form of a tube portion and is secured such that it cannot be rotated. The lateral wall 18 of the ring 17 has slots 19 passing through it in diametrically opposite regions, these slots extending, directed obliquely upward, in the indexing direction and opening out downward in the direction of the annular edge which is directed away from the toothed rim 16.

The toothed rim 16 extends axially approximately over half the height of the ring 17, the lateral wall 18 of which, being stepped in the direction of the annular end edge which is directed away from the toothed rim 16, tapers radially.

Beneath the toothed rim 16, a latching finger 20 is integrally formed on the inside of the lateral wall 18 of the ring 17. This latching finger, as seen in a plan view of the ring, is offset radially inward in relation to the toothed rim 16, and correspondingly engages in a circular space located radially inside the toothed rim 16. Furthermore, the arrangement of the latching finger 20, which is of elastic formation approximately in the vertical direction, is selected such that this finger engages approximately in a horizontal plane defined by the lower peripheral edges of the toothed rim 16.

The diameter of the disk 15, which carries the sun gear 14, is selected to be slightly smaller than the internal diameter of the ring 17 in the region of the toothed rim 16. The sun gear 14 and disk 15 are preferably formed in one piece, from the same material.

The disk 15 has, on its underside, a sawtooth formation 21 which runs around the periphery and in which the latching finger 20 of the ring 17 engages as a retaining member (preventing return rotation).

The sun gear 14 has a coarse toothing formation. Thus, in the exemplary embodiment illustrated, eight sun-gear teeth 22 are distributed uniformly over the circumference of the sun gear 14. As the sun gear rotates, these teeth 22 interact with the planet gear 13, which is disposed in the same plane between the sun gear 14 and the toothed rim 16 of the ring 17.

The planet gear 13 has an axial pin 23 which projects upward on one side, i.e. in the direction away from the disk 15 of the sun gear 14. This axial pin is held in a rotatable manner in a bore 24 in the region of a collar 25 of a scale ring 26, this collar being oriented radially inward in a disk-like manner. The scale ring 26 is provided, on its outer lateral wall, with an encircling graduated scale 27, the graduated scale corresponding in each case to a number of individual rotary steps of the planet gear 13, which advances the scale ring 26. The planet gear additionally meshes with the toothed rim 16 (see FIG. 2), in order to ensure intermediate positions of the scale ring.

The stepwise displacement of the sun gear 14 and/or of the disk 15, which is integrally formed therewith, takes place via step-action indexing fingers 28 which can yield resiliently approximately in the vertical direction. These fingers engage on the underside of the sawtooth formation 21 of the disk 15.

The step-action indexing fingers 28 are located diametrically opposite one another in relation to the main axis x of the step-action indexing mechanism 11 as a whole. For this purpose, a cylindrical central body in the form of a hub 29 with a central axial through-bore 30 is provided in the first instance. The diameter of this through-bore is slightly larger than the external diameter of the cartridge valve tube 5, which is to pass through this through-bore 30.

At the foot end, the hub 29 merges into a radially widened collar 31. Radially projecting guide portions 32 are integrally formed diametrically opposite one another on this collar and, in the region of their free ends in each case, form a guide pin 33, which is positioned in the associated slot 19 of the ring 17. The hub and fingers 28 are located in the interior of the ring 17 and are set back in relation to the base surface of the housing 34.

The step-action indexing fingers 28 each have a horizontal portion rooted on the guide portions 32, leaving the guide pins 33 to project radially outward beyond the horizontal portion. The step-action indexing fingers 28, which project from the horizontal portions, extend directed obliquely upward, with the possible inclusion of an angle of 45 degrees in relation to the horizontal, this angle being adapted to the slope of the slots 19 in the ring 17. The step-action indexing-finger star thus formed is designated S.

The step-action indexing-finger star S, the ring 17, which contains the inner toothed rim 16, the disk 15, which is integrally formed with the sun gear 14, and the scale ring 26 are aligned concentrically in relation to one another along the axis x, the height of the ring 17 being selected such that both the step-action indexing-finger star S and the sun gear 14, together with the disk 15, are accommodated therein.

The entire planet-gear mechanism 12 as well as the step-action indexing-finger star S and the scale ring 26 are accommodated in a cup-like step-action indexing-mechanism housing 34 with an external diameter adapted to the external diameter of the cartridge 3.

The housing 34 has a lateral wall 35. The latter has a viewing window 36 through which it is possible to see the graduated scale 27 of the scale ring 26.

The housing top 37 contains a central aperture 38 which, in the embodiment which is shown in FIGS. 1 to 3, is surrounded by resilient latching tongues 39 which taper conically in the direction of the housing interior. The aperture diameter is adapted to a diameter of a narrowed portion 40 of a collar 41 which projects centrally beyond the opening-side end wall of the cartridge 3 at the opening end and from which the valve tube 5 extends.

The housing base 42 is formed by a separate part. The latter is connected to the housing 34, for example welded or clipped thereto or secured thereon via a press fit, with the above described individual parts of the step-action indexing mechanism being accommodated therein.

The plate-like housing base 42 has a central bore for the through-passage of a spike, e.g. of the valve tube 5. Furthermore, the housing base 42 has formed on it a latching component 44 which, for holding the ring 17 in position, engages in a window-like recess 45 correspondingly formed in the lateral wall 18 of the ring.

Over the same angle region in which the fitting component 44 is disposed on the base, the outer lateral wall of the housing base 42 has a cutout 46. In the installed state, this is associated with the region of the outlet cross-section of the flow channel 10 in the lower annular housing part 7.

Irrespective of the arrangement which is yet to be described with reference to FIGS. 3 and 4, the step-action indexing mechanism 11 basically functions as follows:

The indexing members (step-action indexing-finger star S, ring 17, disk 15, planet gear 13 and scale ring 26) as well as the housing 34 with the housing base 42 are disposed along axes which extend in the longitudinal direction of the housing 34, that is to say of the actuating stroke x-x, in the example also of the cartridge 3. With the exception of the planet gear 13, all the rest of the components of the step-action indexing mechanism 11 are in fact positioned along the longitudinal axis x-x of the cartridge.

The step-action indexing mechanism 11 can be disposed in an extremely straightforward manner correspondingly concentrically within the cross-sectional profile of a component, e.g. the cartridge 3, specifically in the installation space left between the cartridge head 4 and supporting portion 9 of a standard inhaler 2. The step-action indexing mechanism 11 is supported on the end surface of the supporting portion 9 of the inhaler housing 2 by way of the hub 29 of the step-action indexing-finger star S, this hub being mounted centrally in the indexing-mechanism housing 34. The valve tube 5, which passes through the hub 29, provides for additional centering of the step-action indexing-mechanism unit as a whole.

Upon execution of an actuating stroke of the cartridge 3, and associated vertical displacement of the housing 34 in the direction of a supporting portion 9, the indexing-mechanism housing 34 is carried along via the cartridge head 4, this taking place with displacement of the housing 34, of the planet-gear mechanism 12 and of the scale ring 26 relative to the step-action indexing-finger star S, which is supported on a supporting portion, in this case item 9. Consequently, the step-action indexing fingers 28, as they are subjected to stressing, and further assisted by the step-action indexing-finger star S sliding upward with rotary action in the lateral-wall slots 19 of the ring 17, cause the stepwise rotary advancement of the sawtoothed disk 15. At the same time, the sun gear 14 rotates by the same angle. The step-action indexing fingers 28 thereby move out of the oblique position in the direction of a plane oriented perpendicularly to the longitudinal axis x-x.

If the sun gear 14 has, for example, merely eight teeth distributed uniformly over the circumference, it is not necessarily the case that every rotary stepping movement of the sun gear 14 results in a rotary movement of the planet gear 13. Rather, the rotation of the planet gear 13 about its axis, and the accompanying rotary displacement of the scale ring 26, takes place only after a number of individual rotary steps of the sun gear 14. This cumulative function may be more advantageous than 1:1 transmission.

According to the illustration in FIG. 3, in certain cases, the entire step-action indexing mechanism 11 can easily be secured with latching action on a collar 41 by means of the housing 34. In association with the viewing window 36 of an inhaler, this window being located in the housing, the associated portions of the annular housing parts 6 and 7 then likewise have viewing windows 47, 48 which, by virtue of the position selected, directed toward the mouthpiece 8 of the housing 2, are located within the field of vision of the user operating the hand-held unit 1. For securing the step-action indexing mechanism 11 in position, this mechanism is provided with a guide blade 49 which projects radially from the housing 34.

The step-action indexing mechanism 11 is secured with latching action such that, when the cartridge 3 is removed from the housing 2, the step-action indexing mechanism 11 is also pulled out, remaining on the cartridge 3 in the process. This is quite possible, even in the medical sector, as a result of the special construction of the step-action indexing mechanism because, once removed, the step-action indexing mechanism cannot, for all practical purposes, be actuated, that is to say it cannot adjust itself.

As an alternative, it is thus also possible, as is illustrated schematically in FIG. 4, for the step-action indexing mechanism 11 to be latched to the housing 2. For this purpose, during initial assembly, the step-action indexing mechanism 11 passes beyond one or more radially inwardly projecting latching protrusions 51 of the housing 2, which latching protrusions 51 then have collar portions 52, which project radially from the indexing-mechanism housing 34, gripping beneath them. The latching protrusions 51 are positioned, as seen in the vertical direction, so as to ensure the vertical displaceability of the step-action indexing mechanism 11 upon stroke actuation of the cartridge 3. The arrangement selected results in the latching protrusions 51 forming holding-down means which keep the step-action indexing mechanism 11 in the housing 2 when the cartridge 3 is pulled out. It is then also the case that the indexing mechanism cannot adjust itself.

A further embodiment (not illustrated) may provide for a combination of the embodiments according to the illustrations in FIGS. 3 and 4 in which the step-action indexing mechanism 11 is latched on the collar 41 on the cartridge head by means of the resilient latching tongue 39. Such a preassembled cartridge/step-action indexing-mechanism unit is introduced into the housing 2 of the inhaler prior to initial assembly of the latter, collar portions 52 which project radially on the indexing-mechanism housing 34 passing over latching protrusions 51 on the unit housing in a manner corresponding to the second exemplary embodiment, which results in the step-action indexing mechanism 11 being secured definitively in the housing 2. This latching between the step-action indexing mechanism 11 and inhaler housing 2 is selected to be more pronounced than the latching between the step-action indexing mechanism 11 and cartridge 3 and accordingly, if the cartridge 3 is pulled out following initial use, the latching between the cartridge 3 and step-action indexing mechanism 11 is released. The re-insertion of the cartridge 3 is facilitated by a relatively weak resilient latching formation for interacting with the collar 41 on the cartridge head.

Both in the case of the above described embodiment and in the case of the embodiment according to the illustration in FIG. 4, it is possible to release the latching between the unit housing 2 and step-action indexing mechanism 11 following removal of the cartridge 3 from the housing 2.

The illustration in FIG. 4a shows a further embodiment, which builds on the configuration which is shown in FIG. 4. Thus, in order to secure the cartridge 3 further—in addition to conventional clamping of the valve tube 5 in the supporting portion 9 on the hand-held-unit housing—provision is made for the cartridge 3 to be blocked in the region of the upper annular housing part 6. Obliquely downwardly directed restraining fingers 55 thus project from the inner lateral wall of this upper annular housing part 6 and are formed integrally therewith, from the same material. These restraining fingers 55 are positioned such that their free peripheral edges, positioned in relation to the cartridge 3, pass with blocking action into that narrowed region of the cartridge 3 which is formed behind the cartridge head 4, in order to thus block the cartridge 3. Furthermore, the restraining fingers 55 are formed such that, at least when the housing 2 is initially assembled with the cartridge 3, the cartridge head 4 can pass over them. It is also the case with this insertion operation, however, that no counting takes place.

The illustration in FIG. 5 shows a further embodiment. In this embodiment, the cartridge 3 is also secured on the upper inhaler housing part 6 by means of restraining fingers 55. This upper inhaler housing part 6 can be released from the lower housing part 7, which forms the mouthpiece 8, the two housing parts 6 and 7 being separated approximately in the region where the plate-like step-action indexing-mechanism housing 34 is positioned. When the two housing parts 6 and 7 have been put together, they are preferably latched, for which purpose one housing part has a latching nose and the other housing part has a correspondingly placed latching recess.

As a result of this separation being possible, the mouthpiece 8, in particular the angled portion which contains the step portion 9, is easier to clean. This cleaning is further facilitated in that the entire step-action indexing mechanism 11, which is in the form of a compact subassembly, can be removed extremely straightforwardly from the lower housing part 7 and thus passed on for separated cleaning without the risk of any counting steps taking place.

The exemplary embodiment illustrated does not provide any securing means—for example latching protrusions 51 which interact with collar portions 52. Rather, the step-action indexing mechanism 11 as a whole is secured in the lower housing part 7 in conjunction with the cartridge 3 in the use position, with the step-action indexing mechanism 11 being aligned between the supporting portion 9 and the facing end surface of the cartridge head 4 (as is also illustrated with reference to the embodiment which is shown in FIG. 4a). It is also the case that there is no risk of damage during washing, etc., of the removed step-action indexing mechanism.

It is also the case in this embodiment that the step-action indexing mechanism 11 is secured against rotary displacement about the axis x-x by a positive connection between the step-action indexing mechanism 11 and lower housing part 7.

All features disclosed are (in themselves) pertinent to the invention. The disclosure content of the associated/attached priority documents (copy of the prior application) is hereby also included in full in the disclosure of the application, also for the purpose of incorporating features of these documents in claims of the present application.

The invention claimed is:

1. Step-action indexing mechanism, in particular for hand-held units for apportioned delivery of inhaler medicaments, having an annular housing encircled, around its longitudinal axis, by a scale ring which is moved in a stepwise manner by indexing fingers which pivot, counter to spring loading, in the direction of a plane perpendicular to the longitudinal axis of the housing during the actuating stroke and thus via toothed engagement means cause the scale ring to rotate, characterized in that an annular part, which is disposed in a rotationally fixed manner in the housing, has at least one slot which extends obliquely upward from the lower peripheral edge for the insertion of a guide pin of a step-action indexing-finger star, the step-action indexing fingers of which extend from a central hub, in opposite directions, directed obliquely upward in the form of a secant, and, during the actuating stroke, counter to their inherent spring stressing, enter, moving inwardly, into the toothed engagement means in order to rotate the scale ring.

2. Step-action indexing mechanism according to claim 1, characterized in that the scale ring is rotated via a planet-gear mechanism, the planet gear of which is mounted in a bore of the scale ring and the associated sun gear of which is seated on a disk comprising the toothed engagement means which the step-action indexing fingers engage, the planet-gear mechanism passing on the angle of rotation of the disk to the scale ring in stepped-down form.

3. Step-action indexing mechanism according claim 1, characterized in that the hub of the step-action indexing-finger star has a central bore and, by way of its underside end surface, is associated with a supporting portion.

4. Step-action indexing mechanism according to claim 1, characterized in that the axes of all the indexing members are located perpendicularly to the plane of the scale ring.

5. Step-action indexing mechanism according to one claim 1, characterized in that the hub is spaced apart from the underside of the base of the housing.

6. Step-action indexing mechanism according to claim 1, characterized in that the actuating stroke, which is introduced into the housing top, continues via the scale ring, a planet-gear mechanism, and via the toothed engagement means, into the more or less flat-state indexing fingers which, by engaging the toothed engagement means of the disk, rotate the latter, in the process springing over stopping fingers, which prevent return rotation.

7. Step-action indexing mechanism according to one claim 1, characterized by being disposed in a hand-held-unit inhaler such that the step-action indexing-mechanism housing, which is configured as an annular housing, has a central hole, and that the hub has a central bore, for the through-passage of the inhaler valve tube, and is latched on the hand-held-unit housing such that it can still be displaced inward by the actuating stroke, the lower end surface of the hub being supported in the process on the supporting portion, which has a hole.

8. Hand-held appliance for apportioned delivery of inhaler medicaments through the outlet tubule of a cartridge which is displaceable for this purpose against opposed spring loading, characterized by a step-action indexing mechanism according to claim 1 being arranged held on the cartridge and arranged in such a way that the spring loading of the cartridge outlet tubule is aligned for inherent spring loading of the step-action indexing fingers.

* * * * *